United States Patent [19]

McLaughlin

[11] Patent Number: 5,218,723
[45] Date of Patent: Jun. 15, 1993

[54] SURGEON'S CAP AND METHOD OF FABRICATING SAME

[76] Inventor: James G. McLaughlin, 4103 Kenwood Dr., Huntsville, Ala. 35801

[21] Appl. No.: 760,605

[22] Filed: Sep. 16, 1991

Related U.S. Application Data

[63] Continuation-in-part of Ser. No. 415,658, Oct. 2, 1989, Pat. No. 5,048,126.

[51] Int. Cl.$^5$ .......................... A41D 13/08; A42B 1/00
[52] U.S. Cl. ...................................... 2/243 B; 2/270; 2/125; 2/197; 2/200
[58] Field of Search ................ 2/171, 171.5, 183, 197, 2/200, 209.3, 209.4, 243 R, 243 A, 243 B, 410, 417–420, DIG. 7, 125

[56] References Cited

U.S. PATENT DOCUMENTS

| | | | |
|---|---|---|---|
| 1,899,022 | 2/1933 | Duisdieker | 2/243 B X |
| 2,627,126 | 2/1953 | France | 36/9 A |
| 2,707,284 | 5/1955 | Artzt | 2/243 B |
| 3,015,106 | 1/1962 | Van Moer | 2/243 R X |
| 3,187,345 | 6/1965 | Holford | 2/192 X |
| 3,359,658 | 12/1967 | Price | 36/9 R X |
| 3,490,077 | 1/1970 | Brown | 2/243 R |
| 3,657,741 | 4/1972 | Blanco | 2/59 |
| 3,696,445 | 10/1972 | Craig | 2/243 R |
| 3,699,591 | 10/1972 | Breitkopf et al. | 2/243 R |
| 3,710,396 | 1/1973 | Tomlinson | 2/197 X |
| 3,719,955 | 3/1973 | Hrubecky | 2/243 R |
| 3,798,503 | 3/1974 | Larsh et al. | 36/9 A X |
| 4,007,835 | 2/1977 | Klothe | 2/274 X |
| 4,407,284 | 10/1983 | Pieniak | 2/270 X |
| 4,480,772 | 11/1984 | Lant | 2/200 X |
| 4,493,116 | 1/1985 | Niethammer et al. | 2/243 B X |
| 4,523,336 | 6/1985 | Truman | 2/243 R X |
| 4,532,655 | 8/1985 | Bowditch | 2/125 X |
| 4,642,819 | 2/1987 | Ales et al. | 2/270 X |
| 4,691,390 | 9/1987 | McKeown | 2/243 B X |
| 4,825,564 | 5/1989 | Sorce | 36/9 R X |
| 4,842,666 | 6/1989 | Werenicz | 156/161 |
| 5,048,126 | 9/1991 | McLaughlin | 2/125 |

FOREIGN PATENT DOCUMENTS

| | | | |
|---|---|---|---|
| 663549 | 11/1959 | Canada | 2/243 R |
| 1460303 | 12/1965 | France | 2/DIG. 7 |
| 2188438 | 1/1974 | France | 2/243 R |
| 137775 | 1/1920 | United Kingdom | 2/243 R |
| 962355 | 7/1964 | United Kingdom | 2/200 |

Primary Examiner—Thomas B. Will
Assistant Examiner—Scott W. Cummings
Attorney, Agent, or Firm—Hopkins & Thomas

[57] ABSTRACT

An improved method of fabricating disposable coverings such as surgeon's caps comprises applying elastic strips and adhesive along opposed edges of two lengths of sheet material, folding and securing the edges over the elastic strips, applying spaced elastic strips and adhesive along and straddling the center line of one of the lengths of sheet material, bringing the sheets together and securing them along their center lines with the applied adhesive, cutting the sheets apart along their center lines to produce two sub-lengths of material, and cutting and heat sealing the sub-lengths at spaced intervals across their lengths to produce disposable surgeon's caps. The invention also contemplates a disposable protective covering fabricated by this method.

7 Claims, 4 Drawing Sheets

SURGEON'S CAP AND METHOD OF FABRICATING SAME

REFERENCE TO RELATED APPLICATION

This application is a continuation-in-part of U.S. patent application Ser. No. 07/415,658 filed Oct. 2, 1989 now U.S. Pat. No. 5,048,126.

FIELD OF THE INVENTION

The present invention relates generally to protective clothing and particularly to a disposable protective surgeon's cap and to a method of fabricating such a cap.

BACKGROUND OF THE INVENTION

Surgeons, food service workers, and others who work in areas where contamination must be minimized, have long worn protective caps to contain their hair. For many years, such caps were fabricated of cotton and other reusable material such that one cap could be used many times. More recently, however, such caps have been made of lightweight inexpensive non-woven materials such as Nomex. Such materials are so inexpensive that protective caps and other items made therefrom can be used once and simply discarded.

In the past, the fabrication of disposable surgeon's caps has generally involved cutting circular blanks from a sheet of non-woven material and hand sewing an elastic strip around the perimeter of the blanks to produce the finished caps. While this method of producing surgeon's caps has been somewhat successful, it nevertheless has been plagued with numerous inherent problems and shortcomings. For example, since circular blanks are used, the non-woven material between the cut-out circles is typically unsuitable for any commercial purposes and is often discarded after the circles have been extracted. More importantly, however, no satisfactory method has yet been developed for automating the process of sewing the elastic strip around the perimeter of the blanks and manual stitching with a sewing machine is commonly employed. Present methods of producing these caps, therefore, are highly labor intensive with the result that the caps are often fabricated in third-world countries where labor is extremely inexpensive. Even with inexpensive labor, the manual sewing process is still inherently inefficient such that a large labor force is usually required to produce caps in reasonable commercial quantities.

Accordingly, a continuing and heretofore unaddressed need exists for an efficient automated method of fabricating disposal surgeon's caps that eliminates the need for a manual labor force and that produces caps of consistent high quality and unique design in commercially usable quantities. It is to the provision of such a method and a cap produced by the method that the present invention is primarily directed.

SUMMARY OF THE INVENTION

Briefly described, the present invention comprises a method of fabricating surgeon's caps from non-woven materials such as Nomex. Obviously, while the invention will be described herein with reference to the fabrication of caps, it will be understood by persons of skill in the art that the method disclosed herein might also apply to the fabrication of other types of disposable garments such as beard covers, shoe covers, and the like. The selection of a cap as illustrative of a preferred embodiment of the invention should therefore not be construed as a limitation of the invention.

In one preferred embodiment, the method of this invention comprises providing first and second lengths of heat sealable sheet material such as non-woven Nomex having opposed parallel edges and being of substantially the same width. Elastic strips are applied along the edges of each length of sheet material and the edges are folded over the elastic strips and are secured in place with adhesive. A pair of spaced elastic strips are then applied to the first length of sheet material along its length and preferably straddling its center line. Adhesive is then applied along the center of the first length of sheet material covering the spaced elastic strips and the two lengths of sheet material are aligned and brought and pressed together so that they become joined by the applied adhesive along their center lines and in the region of the spaced elastic strips. The two lengths of material are then cut apart along their center lines and between the spaced elastic strips whereupon each of the resulting sub-lengths of material is cut and heat sealed at spaced intervals across its length to produce the protective coverings of the present invention.

Thus, a method of fabricating protective coverings such as surgeon's caps is now provided wherein the caps can be produced by fully automated high-speed processes. As a result, the caps are of consistent high quality and can be fabricated at a fraction of the cost of prior art manual processes. Further, the caps themselves are unique and superior to prior art caps because they are formed with an elastic seal at their top, which expands readily to accommodate and conform to various hair styles of individuals wearing the cap.

These and other features, objects, and advantages of the present invention will become more apparent upon review of the following detailed description taken in conjunction with the accompanying drawings.

DETAILED DESCRIPTION OF THE PREFERRED EMBODIMENTS

Figure 1B:
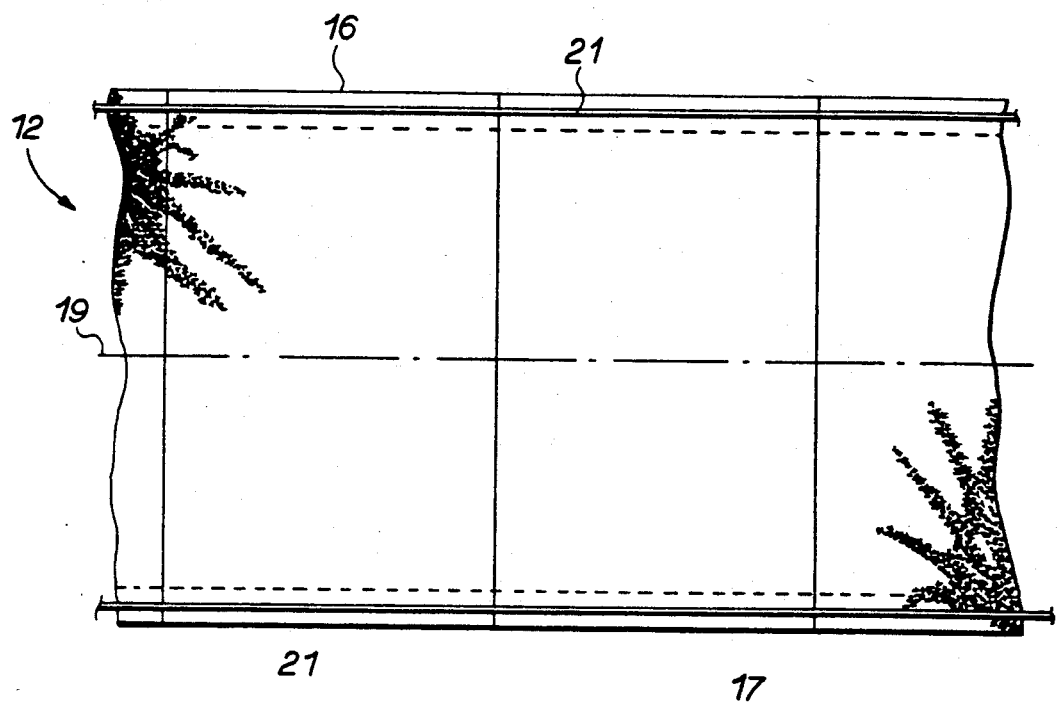
FIGS. 1A and 1B show preferred positioning of elastic strips on the first and second lengths of non-woven sheet material.
Figure 1A:
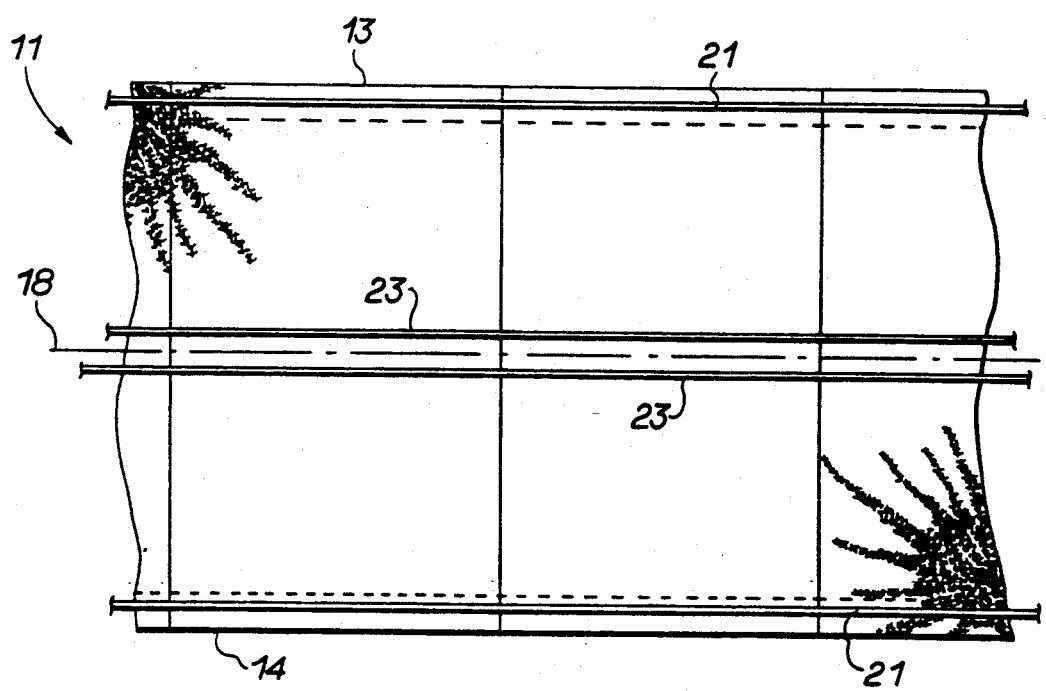

Referring now in more detail to the drawings, in which like numerals represent like parts throughout the several views, FIGS. 1A and 1B illustrate two lengths of sheet material from which protective coverings can be fabricated according to the present invention. The first and second sheets, 11 and 12 respectively, are preferably of a non-woven synthetic heat sealable material such as, for example, Nomex. Such material is preferable because of its low cost, light weight, and superior heat sealing properties. Obviously, other materials might also be used with the method of this invention depending upon specific needs.

The first length of material 11 is seen to have opposed parallel edges 13 and 14 and the second length of material 12 has opposed parallel edges 16 and 17. Respective center lines 18 and 19 are indicated in FIGS. 1A and 1B for clarity of illustration.

Figure 2A:
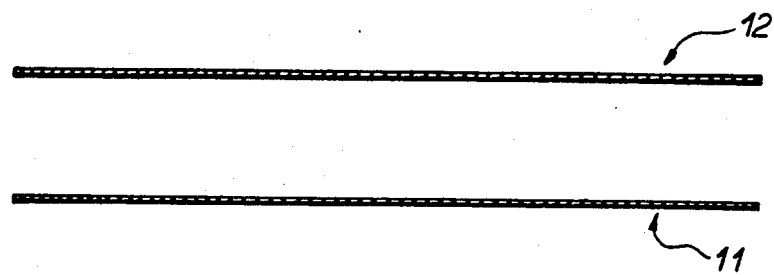
FIGS. 2A through 2F illustrate a preferred sequence of steps for carrying out the method of this invention.
Figure 2B:
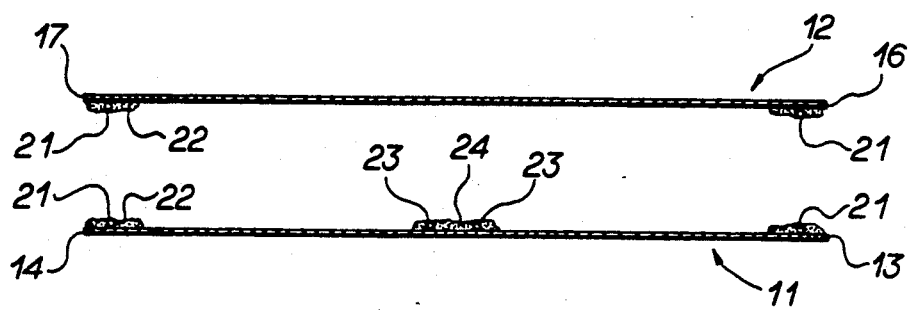
Figure 2C:
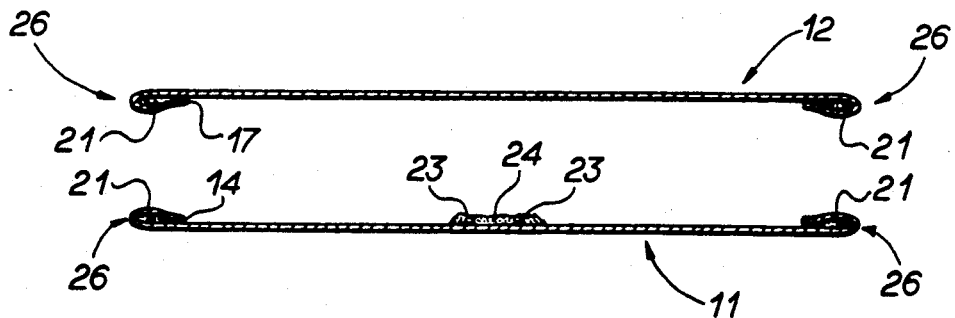

Referring principally to FIGS. 2A–2F, the method of this invention comprises providing first and second lengths of sheet material 11 and 12. Next, elastic strips 21 are applied to the first and second lengths of material along and adjacent to their edges as best illustrated in FIGS. 1 and 2B. While elastic strips 21 can be formed of any of a number of stretchable materials, elastic threads, commonly known as lycra, have been found to be preferable because of their substantially linear and superior elasticity characteristics. Such threads are also small and typically inexpensive relatively to other types of elastic strips that may be used.

With elastic strips 21 applied along the edges of the two lengths of material, a contact or fibrous adhesive 22 is applied, preferably by spray nozzle, along the edges of the lengths of material and covering the elastic strips. A pair of spaced elastic strips 23 and corresponding adhesive 24 is applied to the first length of sheet material 11 along the center line thereof with the elastic strips 23 straddling the center line and with the adhesive applied along a path that spans the center line and overlies the elastic strips.

Next, the edges, 13, 14, 16, and 17, of the first and second lengths of sheet material respectively, are folded over the elastic strips 21 to form elastic hems 26 along the edges of the material. After having been folded, each of the edges is preferably pressed into position such that the adhesive 22, previously applied, can bind securely to the folded edges and hold them firmly in place. Further, it will be understood that the adhesive strips 21 and 23 are pre-stretched prior to their application and that the adhesive 23 and 24 also serves to secure the strips in their pre-stretched configuration on the material.

Figure 2D:
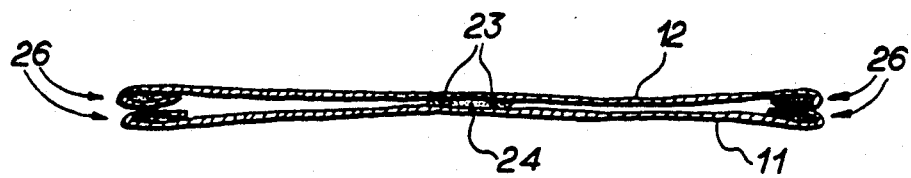

With the elastic hems formed in the first and second lengths of sheet material 11 and 12, the sheets are aligned and brought together as shown in FIG. 2D and preferably pressed along their respective center lines such that the previously applied adhesive along the center of the first length of sheet material 11 can bind securely to the second length of sheet material 12 to join the sheets together along their center lines and along the positions of the spaced elastic strips 23.

Figure 2E:
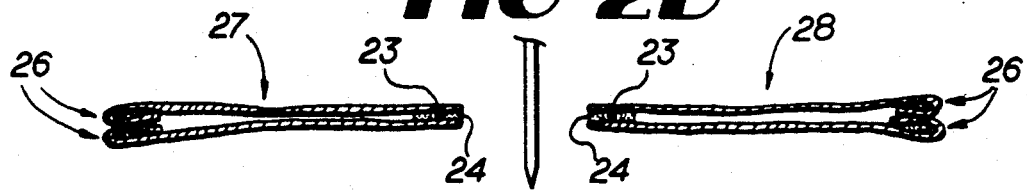
Figure 2F:
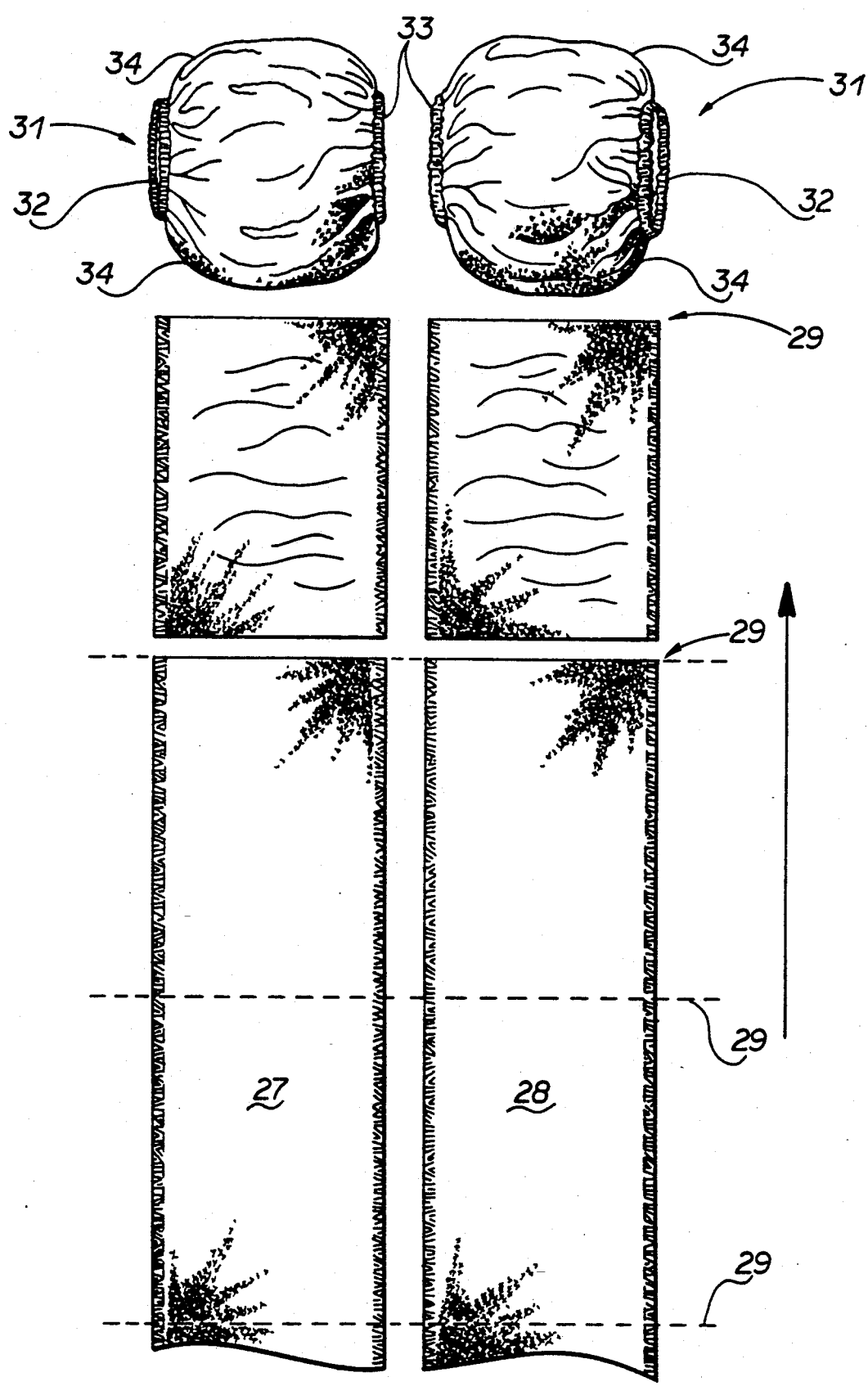

With the lengths of sheet material securely joined along their center lines, they are next cut apart as shown in FIG. 2E substantially along their center lines and in between the spaced elastic strips 24 to separate the lengths of material into two sub-lengths of material 27 and 28 (FIGS. 2E and 2F).

Finally, as illustrated in FIG. 2F, the sub-lengths of material 27 and 28 are cut and sealed at spaced intervals 29 along their length to produce individual protective coverings 31. Preferably, the cutting and sealing of the sub-lengths 27 and 28 is accomplished simultaneously by a hot wire cutter or other suitable device that functions partially to melt the cut edges and thus to heat seal them together along the length of the cut. The resulting caps 31 have open elasticized mouths 32 at their bottoms, closed and sealed elasticized tops 33 and permanently heat sealed side edges 34.

Of course, the lengths of sheet material must be maintained in a tightly stretched configuration after the elastic strips are applied since the pre-stretched strips tend to retract and gather the material along its edges. Once the transverse cuts and seals have been made, however, the resulting caps 31 can be left to gather together naturally under the influence of the elastic strips as shown in FIGS. 2F and 3 prior to being packed for shipment.

Figure 3:
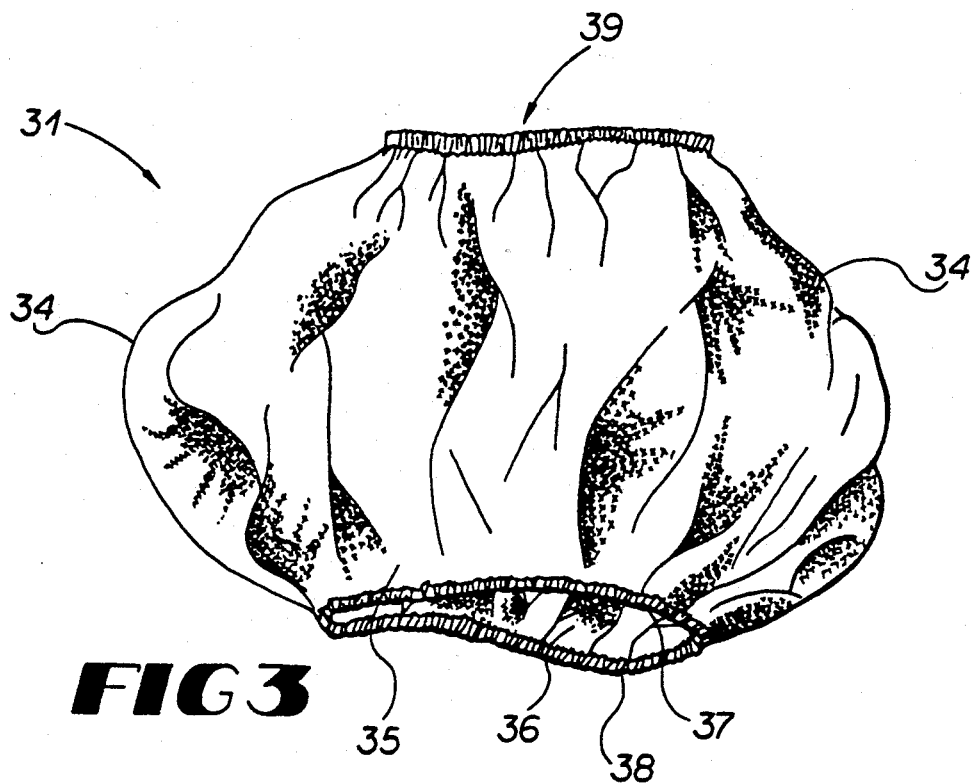
FIG. 3 is a perspective view of a surgeon's cap that embodies principles of the present invention in a preferred form.
Figure 4:
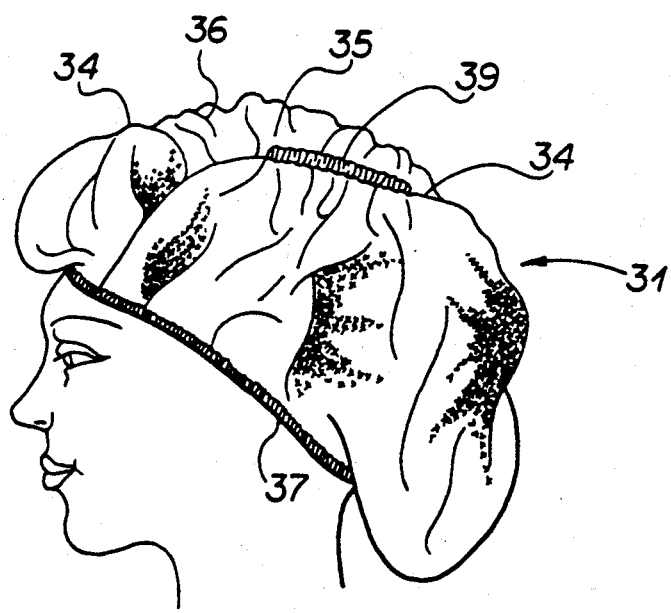
FIG. 4 illustrates the cap of FIG. 3 as it appears on a wearer's head.

FIG. 3 illustrates a disposable surgeon's cap fabricated according to the method of the present invention. Again, while surgeon's caps are illustrated in the preferred embodiment, it will be clear that many other types of protective covers might also be result from application of the method of this invention.

The cap 31 is seen to comprise first and second lengths of sheet material 35 and 36 being disposed in overlying relationship with their corresponding ends 34 being heat sealed together as described above. One edge 37 of the first length of sheet material 35 is formed with an elastic hem and a corresponding edge 38 of the second length of sheet material is also formed with an elastic hem. In this way, the cap 31 forms an open elasticized mouth at its bottom for receiving and conforming to a wearer's head.

The other edges 39 of each of the lengths of sheet material are adhesively secured together with an elastic strip captured between the adhered edges. The top of the cap is therefore closed off and elasticized such that when the cap is placed on a wearer's head, the elasticized top 39 can expand to accommodate and conform to varying styles and quantity of hair. The method of this invention, therefore, results in a surgeon's cap that is superior in configuration and in function to prior art caps.

A primary advantage of the method of this invention is its adaptability to continuous automated manufacturing techniques. The lengths of sheet material, for example, can easily be drawn from large supply rolls and moved along a processing path where the various steps of the invention can be performed sequentially by automated machinery with a minimum of human intervention. The method of the invention can thus be performed economically, even when competing with inexpensive third-world manual labor.

The invention has been described herein in terms of preferred embodiments and methodologies. It will be obvious to those of skill in this art, however, that numerous variations might well be made to the illustrated embodiments within the scope of the present invention. The method has been illustrated, for example, for use in fabricating disposable surgeon's caps. Obviously, many other types of coverings might also be produced with the method of this invention. Further, while non-woven material has been suggested as preferred, the method might also be used with woven or other types of materials and the transverse cut edges might be sealed by a suitable method other than heat sealing. Finally, while adhesive has been illustrated as the preferred method of securing various parts of the cap together, any other appropriate type of securement, such as sewing, ultrasonic bonding, or the like might also be employed. These and many other additions, deletions, and modifications, might well be made to the embodiments illustrated herein without departing from the spirit and scope of the invention as set forth in the claims.

I claim:

1. A method of fabricating a protective covering from heat sealable sheet material with said method comprising the steps of:

(a) providing a first length of the sheet material having a predetermined width and opposed parallel edges;

(b) providing a second length of the sheet material having opposed parallel edges and having a width substantially the same as the width of the first length of sheet material;

(c) applying elastic strips to the first length of sheet material with the elastic strips extending along and adjacent to the opposed edges thereof;

(d) applying elastic strips to the second length of sheet material with the elastic strips extending along and adjacent to the opposed edges thereof;

(e) folding the edges of the first and second lengths of sheet material over their adjacent elastic strips and securing the folded edges in place to form elastic hems along the edges of the first and second lengths of sheet material;

(f) applying a pair of spaced elastic strips to the first length of sheet material with the spaced elastic strips extending longitudinally along the first length of sheet material intermediate its edges;

(g) bringing the first and second lengths of sheet material together in overlying relationship with the edges of the first length of sheet material being substantially aligned with the edges of the second length of sheet material;

(h) securing the second length of sheet material to the first length of sheet material along a longitudinal path that overlies the pair of spaced elastic strips on the first length of sheet material;

(i) cutting the overlying lengths of sheet material apart along a longitudinal path that extends between the spaced elastic strips to separate the sheet material into two sub-lengths; and (j) cutting and sealing the sub-lengths at spaced intervals across their lengths to produce protective coverings.

2. The method of claim 1 and wherein steps (c) and (d) further comprise applying adhesive along the edges of the first and second lengths of sheet material with the adhesive covering the elastic strips whereby the elastic strips are secured in place by the adhesive and the adhesive functions to secure the folded edges in place in step (e).

3. The method of claim 1 and wherein step (f) further comprises applying adhesive to the first length of sheet material along a longitudinal path that overlies the pair of spaced elastic strips thereon whereby the first and second sheets are secured together in step (h) by the adhesive applied in step (f).

4. The method of claim 1 and where in step (j) the sub-lengths are cut by a hot cutter that simultaneously cuts the sub-lengths apart across their lengths and heat seals the cut pieces together at the cuts.

5. The method of claim 1 and wherein step (a) comprises drawing the first and second lengths of sheet material from respective supplies of sheet material.

6. A disposable protective covering of the type commonly worn by surgeons with said protective covering being fabricated of heat sealable sheet material and comprising first and second lengths of sheet material having opposed ends and opposed edges, said first and second lengths of sheet material being disposed in overlying relationship with each of the opposed ends of said first length of sheet material being sealed to a corresponding end of said second length of sheet material, one edge of said first length of sheet material being formed with an elastic hem and a corresponding edge of said second length of sheet material being formed with a corresponding elastic hem to define an open elasticized mouth of said protective covering, the other edges of said first and second lengths of sheet material being sealed together to close off said protective covering at its top, and an elastic strip captured between the secured other edges of said first and second lengths of sheet material whereby the closed off top portion of said protective covering is yieldably gathered together by the captured elastic strip.

7. The disposable protective covering of claim 6 and wherein said opposed ends of said first and second lengths of sheet material are heat sealed together.

* * * * *